(12) United States Patent
McCleary et al.

(10) Patent No.: US 7,273,499 B2
(45) Date of Patent: Sep. 25, 2007

(54) MODULAR TRIAL MECHANISM

(75) Inventors: Larry G. McCleary, Warsaw, IN (US); Farid Bruce Khalili-Araghi, Briarclif Manor, NY (US); Marc Weissman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 633 days.

(21) Appl. No.: 10/260,137

(22) Filed: Sep. 30, 2002

(65) Prior Publication Data
US 2004/0064186 A1    Apr. 1, 2004

(51) Int. Cl.
*A61F 2/30* (2006.01)
*A61F 2/32* (2006.01)

(52) U.S. Cl. ................ 623/18.11; 623/22.42

(58) Field of Classification Search ......... 623/18.11, 623/19.11–19.14, 22.11–22.14, 23.11, 23.15, 623/22.42, 22.15, 22.4, 20.15; 606/86, 85, 606/63, 65
See application file for complete search history.

(56) References Cited

U.S. PATENT DOCUMENTS

| | | | |
|---|---|---|---|
| 3,918,441 A * | 11/1975 | Getscher | 606/64 |
| 4,135,517 A | 1/1979 | Reale | |
| 4,163,292 A | 8/1979 | Averett, Jr. | |
| 4,601,289 A | 7/1986 | Chiarizzio et al. | |
| 4,658,808 A | 4/1987 | Link | |
| 4,908,032 A | 3/1990 | Keller | |
| 4,919,678 A | 4/1990 | Kranz | |
| 4,963,155 A | 10/1990 | Lazzeri et al. | |
| 5,002,578 A | 3/1991 | Luman | |
| 5,032,130 A | 7/1991 | Schelhas et al. | |
| 5,074,879 A | 12/1991 | Pappas et al. | |
| 5,080,685 A * | 1/1992 | Bolesky et al. | 623/22.42 |
| 5,100,407 A | 3/1992 | Conrad et al. | |
| 5,108,437 A | 4/1992 | Kenna | |
| 5,286,260 A | 2/1994 | Bolesky et al. | |
| 5,342,366 A * | 8/1994 | Whiteside et al. | 606/86 |
| 5,507,817 A | 4/1996 | Craig et al. | |
| 5,507,830 A | 4/1996 | DeMane et al. | |
| 5,569,263 A | 10/1996 | Hein | |
| 5,601,567 A | 2/1997 | Swajger et al. | |
| 5,645,607 A * | 7/1997 | Hickey | 623/23.35 |
| 5,653,765 A | 8/1997 | McTighe et al. | |
| 5,702,480 A | 12/1997 | Kropf et al. | |
| 5,766,261 A * | 6/1998 | Neal et al. | 623/21.15 |
| 5,800,556 A | 9/1998 | Sanders et al. | |
| 5,860,982 A * | 1/1999 | Ro et al. | 606/102 |

(Continued)

FOREIGN PATENT DOCUMENTS

EP    0 558 203    9/1993

(Continued)

*Primary Examiner*—Pedro Philogene
(74) *Attorney, Agent, or Firm*—Maginot, Moore & Beck

(57) ABSTRACT

A prosthetic trial for a joint prosthesis includes a stem having a proximal section and a distal section for implantation in a bone. A body includes a channel receiving at least the proximal section of the stem. A locking mechanism is at least partially disposed within the body. The locking mechanism is biased into a locking position in which the mechanism locks the stem within the first channel of the body. The locking mechanism is accessible outside said body to be pulled into a releasing position to unlock the stem from the body.

28 Claims, 15 Drawing Sheets

U.S. PATENT DOCUMENTS

| | | |
|---|---|---|
| 5,876,459 A | 3/1999 | Powell |
| 5,888,208 A * | 3/1999 | Ro .................... 623/23.15 |
| 5,902,340 A | 5/1999 | White et al. |
| 5,906,644 A * | 5/1999 | Powell ................. 623/20.15 |
| 6,193,759 B1 * | 2/2001 | Ro et al. ............... 623/23.28 |
| 6,206,884 B1 | 3/2001 | Masini |
| 6,264,699 B1 | 7/2001 | Noiles et al. |
| 6,299,648 B1 | 10/2001 | Doubler et al. |
| 6,319,286 B1 | 11/2001 | Fernandez et al. |
| 6,355,068 B1 | 3/2002 | Doubler et al. |
| 6,361,563 B2 * | 3/2002 | Terrill-Grisoni et al. . 623/20.11 |
| 6,428,578 B2 | 8/2002 | White |
| 6,432,110 B1 | 8/2002 | Richelsoph |
| 6,440,171 B1 * | 8/2002 | Doubler et al. .......... 623/22.42 |
| 6,494,913 B1 * | 12/2002 | Huebner ................ 623/19.11 |
| 6,589,282 B2 * | 7/2003 | Pearl .................... 623/19.14 |
| 6,676,706 B1 * | 1/2004 | Mears et al. ............. 623/22.4 |
| 6,875,239 B2 * | 4/2005 | Gerbec et al. ........... 623/23.15 |

FOREIGN PATENT DOCUMENTS

| | | |
|---|---|---|
| FR | 2 660 857 | 10/1991 |
| FR | 2 796 267 | 1/2001 |
| WO | WO 01/82843 | 11/2001 |

* cited by examiner

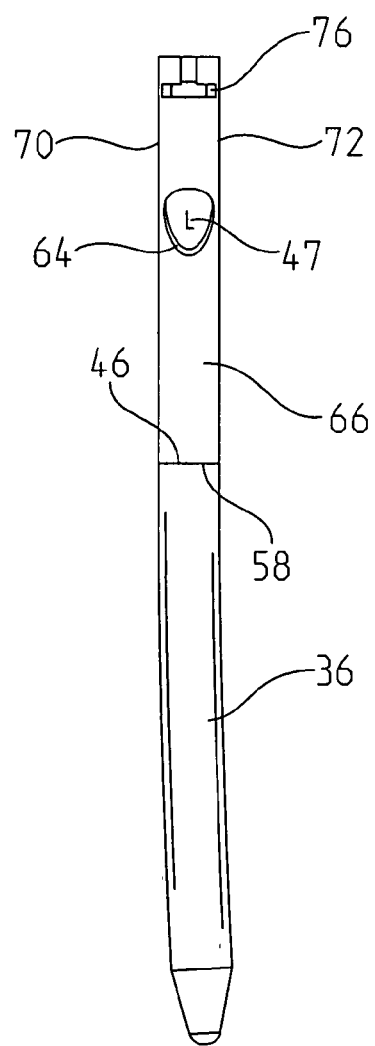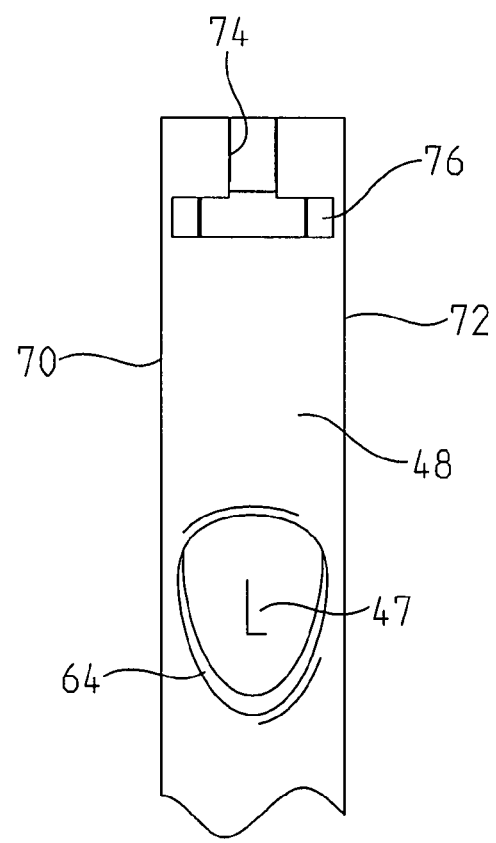
FIG. 6
FIG. 7

MODULAR TRIAL MECHANISM

TECHNICAL FIELD OF THE INVENTION

The present invention relates generally to a surgical trial instrument assembly and, more particularly, to a surgical trial instrument assembly for determining the required dimensions of a prosthetic femoral component.

BACKGROUND OF THE INVENTION

During the lifetime of a patient, it may be necessary to perform a joint replacement procedure or anthroplasty on the patient as a result of, for example, disease or trauma. One such type of joint replacement procedure is a hip replacement procedure in which a diseased and/or damaged hip joint is replaced with a prosthetic hip joint. A typical hip replacement procedure utilizes a prosthesis that generally includes a femoral stem component, a proximal body component, and a neck segment. The femoral stem is implanted in a prepared medullary canal of the patient's femur.

During performance of such a hip replacement procedure, the surgeon must evaluate the size and condition of the patient's bones (e.g. the patient's femur) in order to determine the proper type and configuration of each of the various types of prosthetic components that are to be implanted. One or more provisional components are temporarily fixed to a bone prior to permanent fixation of the prosthetic joint. The provisional components are intended to mimic certain aspects of the permanent prosthetic joint in order for a surgeon to validate measurements and to test several different possible component sizes and shapes. Hence, provisional components are aptly known as "trials", and the procedure is known as "trialing."

Currently, in a majority of revision total hip arthroplasties, the bone has little or no supportive metaphysis or diaphyseal areas. This makes it difficult for surgeons to reproduce the proper anatomy. To do this, the surgeon may use a distally fixed implant. This facilitates trialing from the distal femoral cortex and subsequent proximal anatomy. Many trials are used in surgery having one basic anterior/posterior proximal anatomical body with altering characteristics (i.e., stem lengths, bow, offsets, neck lengths, neck anteversion). Each instance requires a single monolithic trial that duplicates the implant, which is therein made from casting substrate.

Other modular devices contain modular similarities but may not address multi-functional characteristics as per using both neck segments and distal stem variations simultaneously. They also may not use preexisting broach system neck segments and its instrumentation technology to simplify case sizing.

Other techniques require that the broach be removed from the medullary canal to allow the use of a trial having a stem portion, a head and a neck. For example, U.S. Pat. No. 5,100,407 discloses a system including a group of variously sized trial neck/body portions and a group of differing length trial stem portions which are mixed and matched to create a suitable trial. However, repetitive removal and insertion of successions of trial stems accompanied by successive assembly and disassembly with respect to the body can require more time, which will increase operating room cost.

Another known trial includes a stem to which a collar is secured at successive points along the length of the trial until an appropriate neck length and stem length have been ascertained. Undesirably, this type of trial induces measurement inaccuracies resulting from stem movement as the collar is repeatedly engaged and disengaged from the stem. Additionally, as the collar is moved toward the distal end of the stem, less of the stem is disposed within the medullary canal, causing the trial to become increasingly unstable and rendering accurate measurements difficult to achieve.

Any additional anatomical complexity can increase the undesirable numbers of trial components in a kit. For example, trials for long hip stems must be different for the right and left femur due to the curvature or bow of the respective femurs. In other words, a long left stem trial cannot be used in the right femur and vice versa. It is believed that a trial system consisting of numerous parts that must be selected and mated in various combinations, possibly many times, is cumbersome.

Another example, U.S. Pat. No. 6,193,759, uses two component embodiments but has not included an additional neck segment component that encompasses different geometries. The '759 patent does not address the ability to be used on one single broaching system. The system of the '759 patent also does not used the same instrument system to implant or extract both the broach and trial.

Because many variations in sizes and shapes of trials are required to be available to the surgeon, it is necessary to maintain a large inventory of trials and/or trial components. Such a large inventory is costly, occupies valuable operating room space, and is difficult to manage. Another problem is that if a trial is to be assembled from multiple components, the assembly and disassembly of the trial can consume large periods of operating room time.

What is needed therefore is a femur implant trial that can be quickly and easily assembled and disassembled from multiple components.

What is further needed therefore is an apparatus and method for assembling various sizes and shapes of trials from a minimum number of components to be kept in inventory.

SUMMARY OF THE INVENTION

The present invention provides a modular trial assembly that can be assembled, with a minimum inventory of trial components, to mimic many different variations of prosthetic sizes and shapes. The modular trial assembly can be quickly and easily assembled from the trial components.

The present invention reduces the amount of trial sizes by using one proximal body and varying neck and stem component geometry. It also potentially reduces production cost by being made of lower grade stainless steel. The present invention also potentially reduces the sterilization case weight. The trial system of the present invention can be aligned and removed by the same extraction instrument used on the subsequent broaching system, simplifying the overall system. The trial system also uses neck segments used on a subsequent broaching system that has different styles of proximal head configurations.

The prosthetic trial of the present invention includes a proximal body portion that engages the distal stem portion, allowing for different lengths of stem geometry. A single distal stem portion can be curved and reversibly secured to the proximal body portion to provide a long stem trial suitable for either the right or left femur.

In accordance with one embodiment of the present invention, there is provided a prosthetic trial for a joint prosthesis. The trial includes a stem having a proximal section and a distal section for implantation in a bore. A body includes a channel receiving at least the proximal section of the stem. A locking mechanism is at least partially disposed within the body. The locking mechanism is biased into a locking position in which the mechanism locks the stem within the first channel of the body. The locking mechanism is accessible outside said body to be pulled into a releasing position to unlock the stem from the body.

In accordance with another embodiment of the present invention, there is provided a prosthetic trial for a joint prosthesis. The trial includes a neck having one of a first projection and a first recess. The neck also has one of a second projection and a second recess. A body assembly includes the other of the first projection and the first recess. The other of the first projection and the first recess is coupled to the one of a first projection and a first recess. The body assembly also includes another of the second projection and the second recess. The other of the second projection and the second recess is coupled to the one of a second projection and a second recess such that the neck and the body are nonrotatable relative to each other. A stem is detachably connected to the body assembly.

In accordance with yet another embodiment of the present invention, there is provided a prosthetic trial for a joint prosthesis. The trial includes a body, a stem separate from the body, a neck separate from the body and the stem, and a locking mechanism at least partially disposed within the body. The locking mechanism locks the stem to the body and unattachably couples the neck to the body.

An advantage of the present invention is that many variations of sizes and shapes of trials can be assembled from a small number of trial components that are kept in inventory.

Another advantage is that a trial can be quickly and easily assembled from trial components, thereby saving operating room time.

The above and other features and advantages of the present invention will become apparent from the following description and the attached drawings.

BRIEF DESCRIPTION OF THE DRAWINGS

FIG. 6 is a side view of the body and stem of FIG. 1 in an assembled state;

FIG. 7 is an enlarged, fragmentary, side view of the body and stem of FIG. 1 in an assembled state;

DETAILED DESCRIPTION OF THE INVENTION

Figure 1:
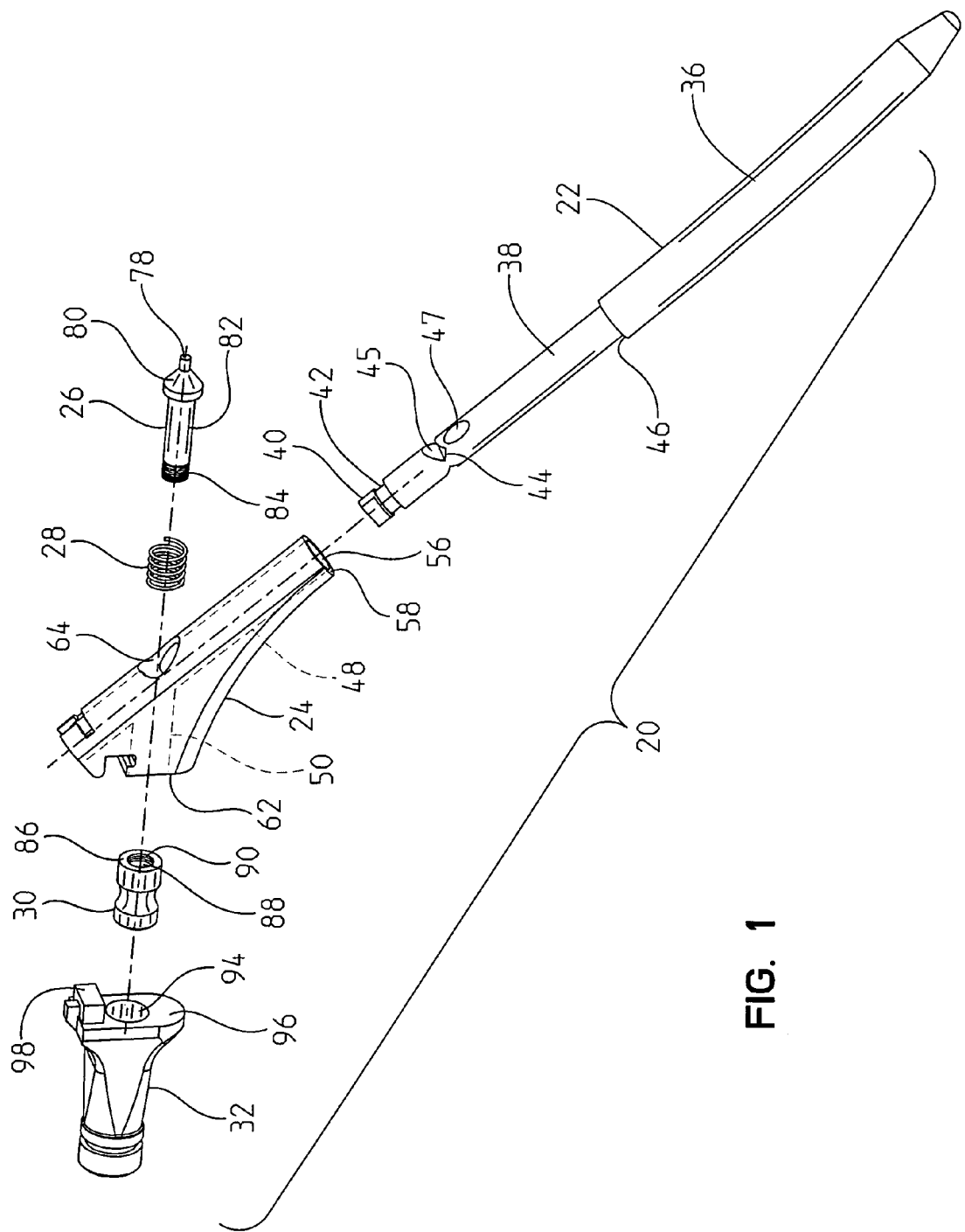
FIG. 1 is an exploded, partially sectional, perspective view of one embodiment of a modular trial assembly incorporating features in accordance with the principles of the present invention.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

It should initially be appreciated that the present invention can be used after proper resection of a patient's proximal femur for evaluating the size and shape of an implant therefor prior to committing to the final preparation of the proximal femur. The proximal end portion of the patient's femur can be resected by use of, for example, a bone saw (not shown). Proper resection of the proximal femur is beyond the scope of the present disclosure. Reference should be made to an appropriate surgical manual for such resection.

Referring now to FIG. 1, there is shown a modular trial assembly 20 according to one embodiment of the invention, including a distal stem 22, a main body 24, a plunger 26, a coil spring 28, a stud 30 and a neck segment 32. The stem 22 is separate from the body 24, and the neck 32 is separate from the body 24 and the stem 22. The plunger 26, the coil spring 28 and the stud 30 together form a locking mechanism. The body 24 and the locking mechanism together form a body assembly. The trial assembly 20 can preferably be made of stainless steel. However, it is possible to form the trial assembly 20 of other materials, such as titanium, cobalt, etc.

Figure 2:
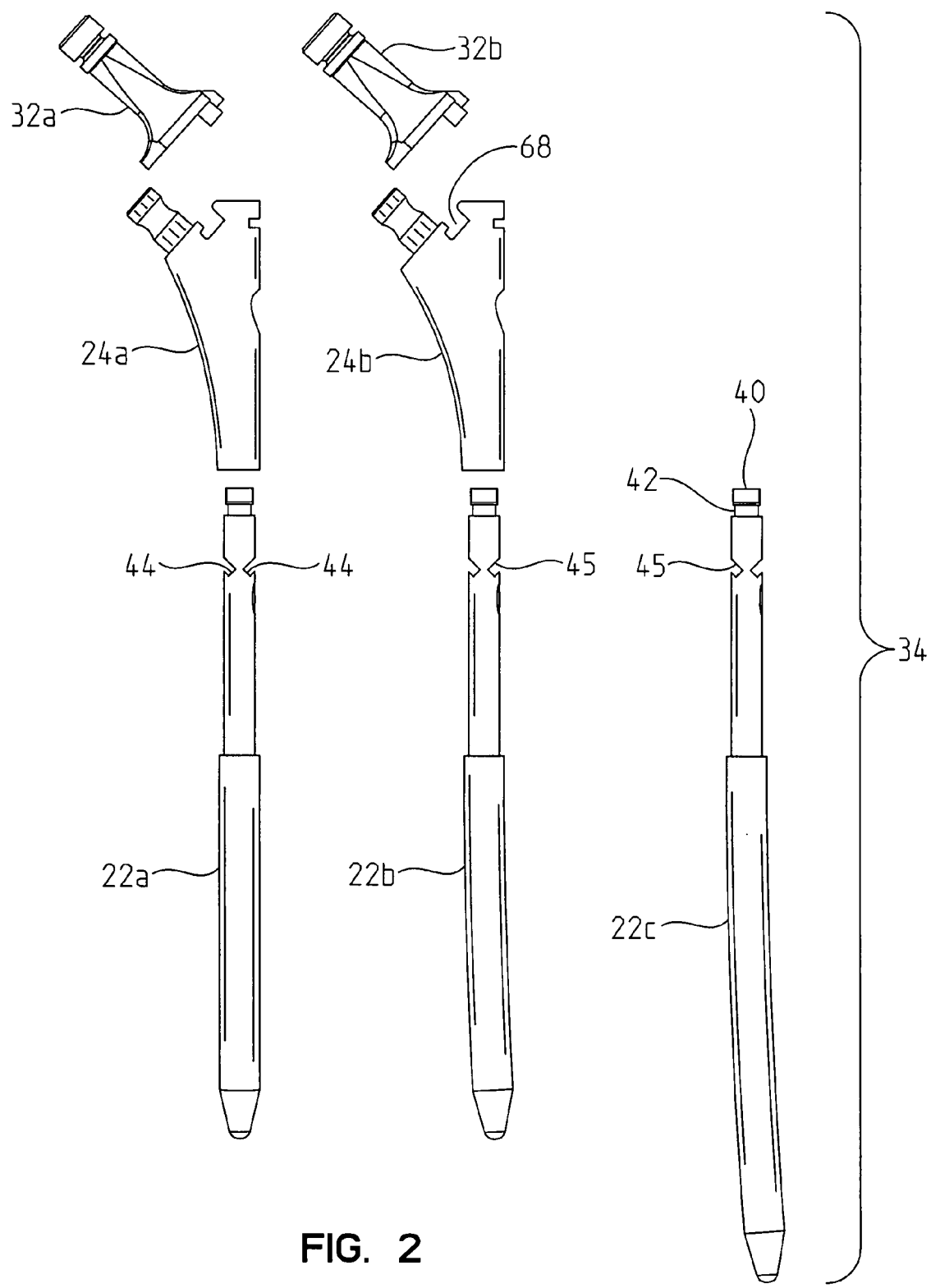
FIG. 2 is a front view of one embodiment of a modular trial assembly kit from which the modular trial assembly of FIG. 1 can be assembled in accordance with the principles of the present invention.

As shown in FIG. 2, a trial system kit 34 can include multiple sizes of each of the distal stem 22, the main body 24 and the neck segment 32. More particularly, the kit 34 can include a small neck 32a, a large neck 32b, a small body 24a, a large body 24b, two small stems 22a, 22b, and a large stem 22c. The kit 34 can also include multiple shapes of the stem 22. For instance, the stem 22a is straight while the stems 22b and 22c are bowed. Thus, different sizes and shapes of the stem 22, the body 24 and the neck 32 can be mixed and matched with one another to produce a modular trial assembly 20 that matches the size and shape of the patient's joint anatomy. Various trial assemblies may be tried in order to ascertain which final implant will work best, in the surgeon's judgment. Regardless of which combination of necks 32, bodies 24 and stems 22 is used to assemble the modular trial assembly 20, the manner of assembly, which will be discussed in detail herein, is substantially the same.

Returning to FIG. 1, the stem 22 includes a distal section 36 and a cylindrical proximal section 38. The distal section 36 is configured for implantation in a bore of a femur. The distal section 36 has a size and shape that is substantially the same as that of the implant for which the distal section 36 trials.

The proximal section 38 includes a key element in the form of a tang 40, an annular groove 42, and two opposing recesses in the form of slots 44. Each slot 44 has a cross section with two right angles, as shown in FIG. 2. However, it is also possible for the slots 44 to have various cross-sectional shapes, such as V-shaped, U-shaped, etc. Each slot 44 is oriented generally perpendicular to the tang 40. An upper side 45 of the slot 44 is oriented at an angle of approximately 45° relative to the longitudinal axis of the stem 22. The proximal section 38 has a diameter than is less than the diameter of the distal section 36, thereby forming an annular shoulder 46 at their junction. Two stem anatomical references in the form of inscriptions 47 are provided on the outer surface of the proximal section 38, with one inscription 47 being below each of slots 44. Each of the inscriptions 47 can identify the stem 22 as being one of stems 22a, 22b and 22c, i.e., identifies the size and shape of the stem 22.

The body 24 includes two intersecting through channels 48 and 50 oriented at an angle of approximately 45° relative to each other. The channel 48 has a rectangular opening 52, best seen in FIG. 3, at a proximal end 54 of the body 24. The channel 48 also has a distal opening 56 at a distal end 58 of the body 24. The channel 48 is sized to receive the proximal section 38 of the stem 22. The proximal opening 52 is configured to receive the tang 40 of the stem 22.

The channel 50 is oriented parallel to the longitudinal axis of the neck 32. The channel 50 has an opening 60, best seen in FIG. 4, at a medial side 62 of the body 24. The medial side 62 is oriented at an angle of 45° relative to the channel 48 and is oriented perpendicular to the channel 50. This orientation allows the medial side 62 to interface with the neck 32. An annular shoulder 63 disposed in the channel 48 at the medial side 62 of the body 24, and best seen in FIG. 5, defines the opening 60. In one aspect of the invention, the diameter of the opening 60 is smaller than the diameter of the channel 50. The channel 50 also forms an opening 64, best seen in FIGS. 6 and 7, at a lateral side 66 of the body 24. The opening 64 is generally oval because the channel 50 intersects the lateral side 66 at an angle.

Figure 3:
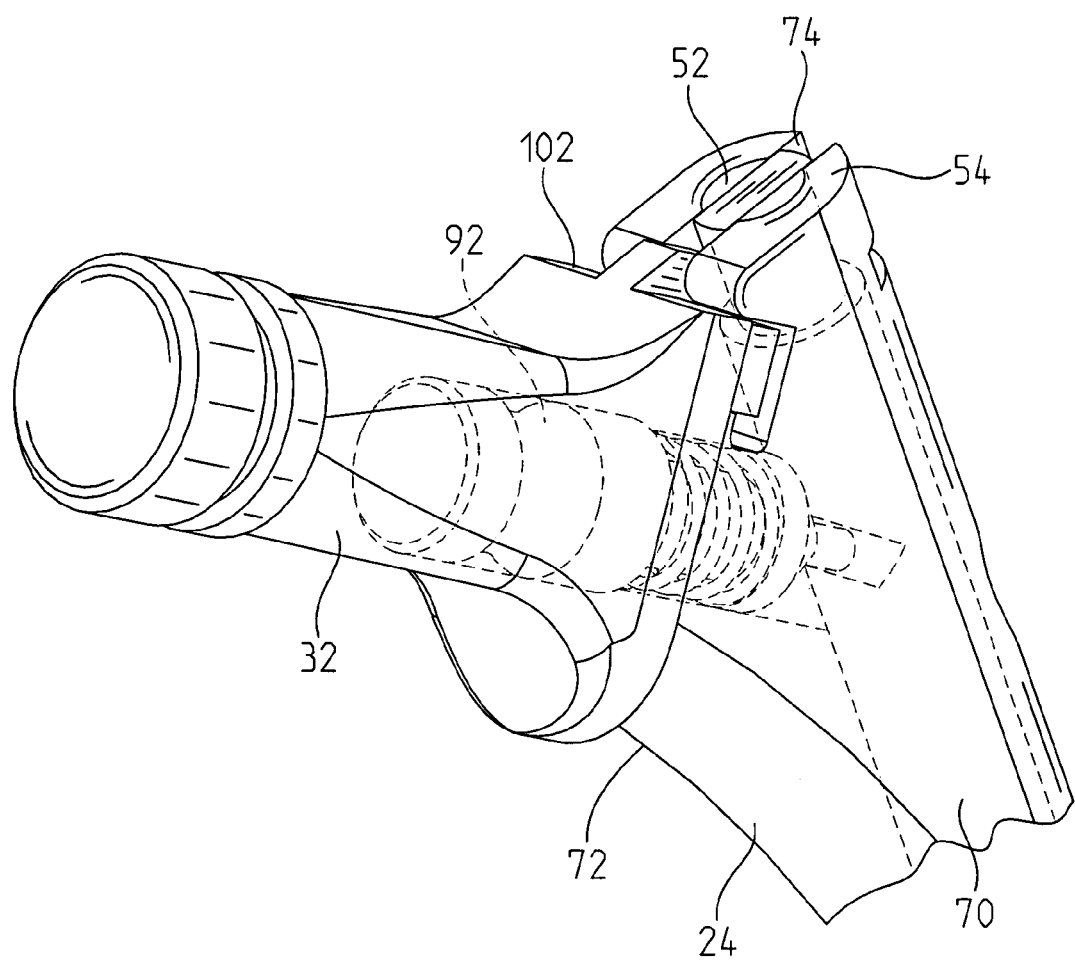
FIG. 3 is a perspective, partially sectional, fragmentary view of the modular trial assembly of FIG. 1 in an assembled state.
Figure 4:
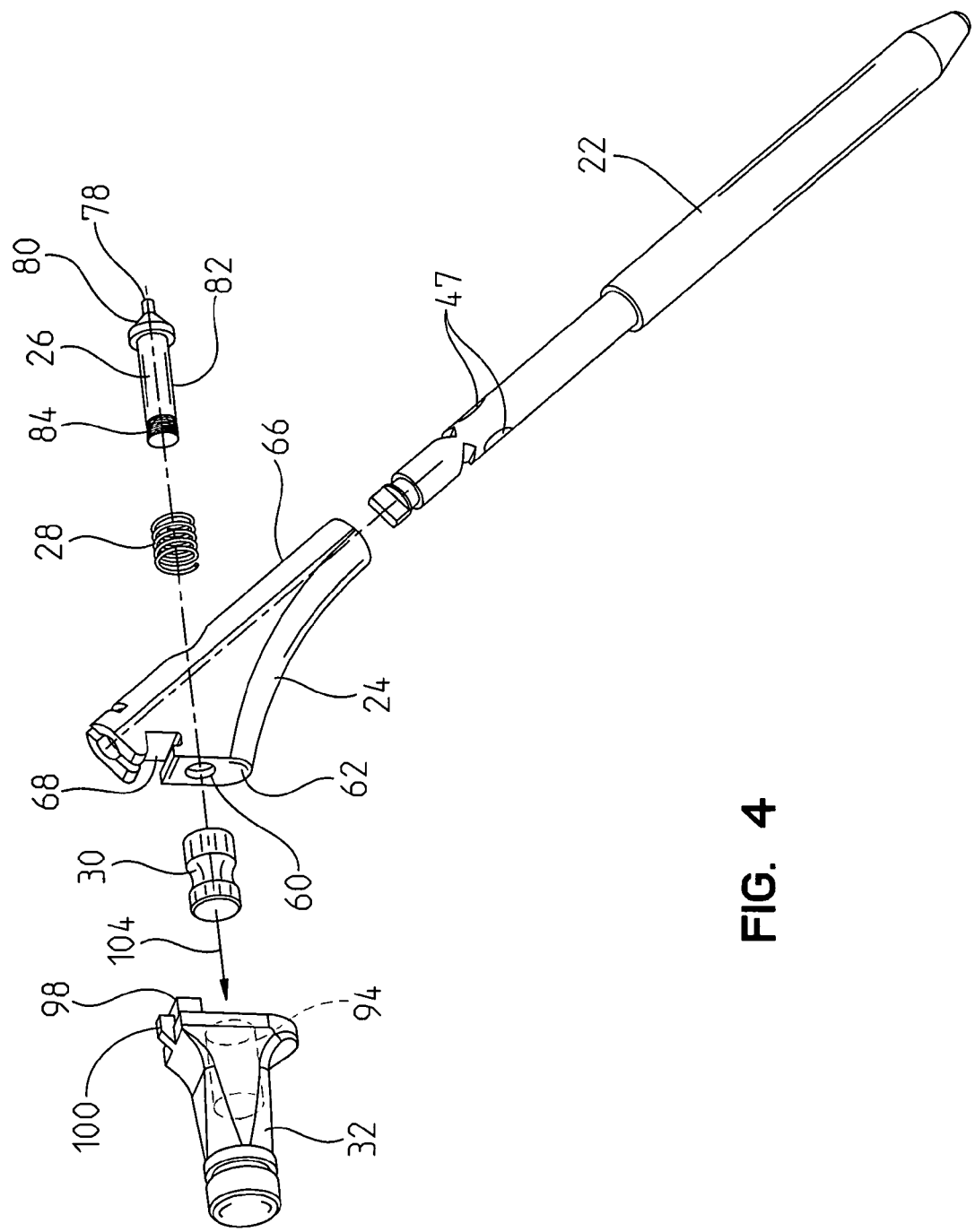
FIG. 4 is another exploded, partially sectional, perspective view of the modular trial assembly of FIG. 1.

The medial side 62 of the body 24 defines an L-shaped slot 68 adjacent the proximal end 54 and extending from an anterior side 70 to a posterior side 72 of the body 24. As shown in FIGS. 3 and 4, the slot 68 is generally perpendicular to the plane defined by the channels 48 and 50. The proximal end 54 of the body 24 also includes a linear slot 74. The slot 74 includes and is an extension of the opening 52 of the channel 48. The slot 74 extends from the lateral side 66 toward the medial side 62 of the body 24, parallel to the plane defined by the channels 48 and 50. The slot 74 is in communication with the channel 48 in order to receive the tang 40 of the stem 22. The slot 74 is also in communication with the L-shaped slot 68 in order for the slot 74 to receive a portion of the neck, as will be discussed in more detail below.

The lateral side 66 of the body 24 includes an arcuate slot 76 (FIG. 7) extending from the anterior side 70 to the posterior side 72 of the body 24, perpendicular to the channel 48. The arcuate slot 76 is in communication with both the linear slot 74 and the channel 48 in order to provide access to the stem 22 when the stem 22 is inserted into the body 24, as will be discussed below.

Looking now at FIGS. 1 and 4, the plunger 26 includes a projection in the form of a pin 78 extending from a head 80. The pin 78 is for insertion into a selected one of the slots 44 of the stem 22. A shaft 82 having exterior threads 84 extends from an opposite side of the head 80. The plunger 26 is sized to fit within the channel 50.

The spring 28 has a diameter greater than the diameter of the shaft 82 but less than the diameter of the head 80. Further, the diameter of the spring 28 is greater than the diameter of the opening 60, and the diameter of the shaft 82 is less than the diameter of the opening 60. Thus, the shaft 82 will pass through the opening 60, but the spring 28 and the head 80 will not pass through the opening 60.

The stud 30 includes a lateral end 86 having a recess 88 with interior threads 90. The outer diameter of the lateral end 86 is greater than the diameter of the opening 60. The threads 90 have a size and spacing that allow the threads 90 to receive the threads 84 of the plunger 26. The outer surface of the stud 30 can include an annular groove 92 to allow an assembler to obtain a firm grip on the stud 30.

The neck segment 32 includes a cylindrical cavity 94 in a lateral surface 96. The cavity 94 is sized to receive the stud 30 therein. The neck segment 32 also includes a block-shaped projection 98 (see FIGS. 1 and 5) extending from the surface 96. Another projection in the form of a fin 100 is disposed partially on an upper surface of the projection 98 and partially on a top surface 102 of the neck segment 32. The fin 100 is oriented parallel to the cavity 94. The projection 98 and the fin 100 are for insertion into the L-shaped slot 68 and the linear slot 74, respectively, to couple the neck 32 to the body 24.

During assembly, the spring 28 is inserted through the opening 64 and into the channel 50. The plunger 26 is then also inserted, threaded end first, through the opening 64 until the threads 84 pass through the spring 28 and through the opening 60. The stud 30 is placed at the position shown in FIG. 1, on the medial side of the opening 60. The stud 30 is then coupled to the plunger 26 by virtue of their mating threads 90 and 84, respectively. Thus, the stud 30 is accessible outside of the body 24.

Once the plunger 26 has been screwed into the stud 30, the surgeon or technician can manually grasp the stud 30 around the groove 92 and pull the stud 30 in a medial direction, as indicated by arrow 104 in FIG. 4. The attached plunger 26 is also pulled in the direction 104 against the bias of the spring 28. As the plunger 26 moves, the head 80 of the plunger 26 compresses the spring 28 against the shoulder 63 on which the spring 28 is seated. The stud 30 is pulled in direction 104 until the plunger 26, including the pin 78, has passed through and is disposed inboard and clear of the channel 48. At this point, the locking mechanism is in a releasing position.

The stem 22, and particularly the portion 38, is then inserted into the channel 48 through the distal opening 56. The stud 30 is held stationary, keeping the plunger 26 out of the channel 48, while the tang 40 and the groove 42 of the proximal section 38 pass by the channel 50. Once the tang 40 has arrived at the proximal opening 52 of the channel 48, the stem 22 is rotated if necessary so that the tang 40 is aligned with and can be inserted into the linear slot 74 at the proximal end 54 of the body 24. One of the inscriptions 47 is visible through the opening 64 when the tang 40 is aligned with and near the slot 74. Thus, the surgeon or technician can look for the inscription 47 through the opening 64 to determine if the tang is properly aligned with the slot 74.

If one of the bowed stems 22b or 22c is being inserted, it must be verified that the bow is oriented in the desired direction before the tang 40 is inserted into the slot 74. If the tang 40 is inserted into the slot 74 with the bow in the wrong direction, the tang 40 must be withdrawn from the slot 74 and the stem rotated 180° before the tang 40 is reinserted into the slot 74. With the tang 40 in the slot 74, the stem 22 is prevented from rotating in the channel 48.

The stud 30 can be released and the lateral end 86 of the stud 30 becomes seated on the shoulder 63. The bias of the spring 28 pushes the plunger 26 in a lateral direction, opposite to the direction 104, until the pin 78 of the plunger 26 is seated in a slot 44 of the stem 22. The pin 78 thus locks, attaches or detachably connects the stem 22 within the body 24. The locking mechanism is now in a locking position.

Figure 5:
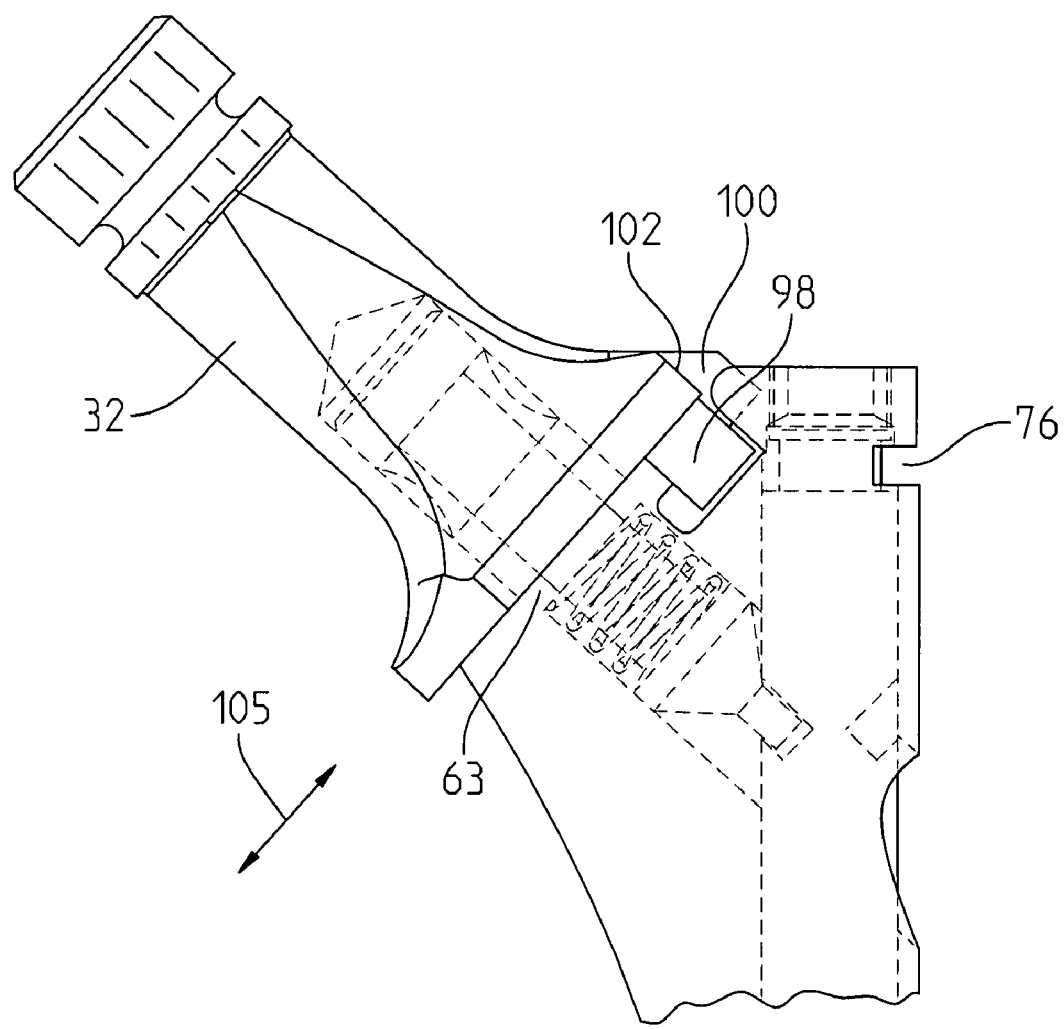
FIG. 5 is a front, partially sectional, fragmentary view of the modular trial assembly of FIG. 1 in an assembled state.

At this point, the groove 42 of the stem 22 is aligned with the slot 76 of the body 24, as best seen in FIG. 5. In addition, the inscription 47 is also visible through the opening 64, as best seen in FIG. 7. Thus, which of the stems 22a, 22b and 22c is locked to the body 24 can be easily discerned by looking at the inscription 47 through the opening 64. The shoulder 46 of the stem 22 is closely adjacent to, and is preferably in contact with, the distal end 58 of the body 24, as best seen in FIG. 6. The diameter of the stem 22 at the shoulder 46 is equal to the diameter of the end 58, thereby forming a seamless junction therebetween, which best mimics the smooth surface of the prosthesis for which the assembly 20 trials.

The neck segment 32 is then placed on and unattachedly coupled to the body 24. What is meant herein by "unattachedly coupled" is that the neck segment 32 is coupled to but not attached to the body 24. For example, a single linear force, such as gravity, exerted on either the neck segment 32 or the body 24, while the other of the neck segment 32 and the body 24 is held stationary, can separate the neck segment 32 from the body 24.

In order to unattachedly couple the neck segment 32 to the body, the cavity 94 of the neck 32 is aligned with the stud 30, and the stud 30 is partially inserted into the cavity 94. The fin 100 of the neck 32 is aligned with the linear slot 74 of the body 24, and the neck 32 is fully pressed onto the body 24. The fin 100 is received in the slot 74, the block-shaped projection 98 is received in the L-shaped slot 68, and the stud 30 is fully received within the cavity 94. With the fin 100 in the slot 74, the neck 32 is prevented from rotating relative to the body 24. The block-shaped projection 98 in the slot 68 prevents the neck 32 from moving in the directions of double arrow 105 in FIG. 5, thereby reducing force exerted on the stud 30 in directions 105 by the neck 32.

The neck 32 is shown as including projections 98, 100 received in recesses 68, 74 on the body 24. However, in another embodiment (not shown), one or both of the projections 98, 100 of the neck are replaced by a respective recess, and one or both of the recesses 68, 74 of the body are replaced by a respective projection received in the corresponding recess of the neck. In general, whether one or both of the projections are placed on the neck or are placed on the body is arbitrary. So long as there are at least two projections and corresponding recesses on the neck and body, the neck and body will not be able to rotate relative to each other, and the neck can be unattachedly coupled to the body.

Figure 8:
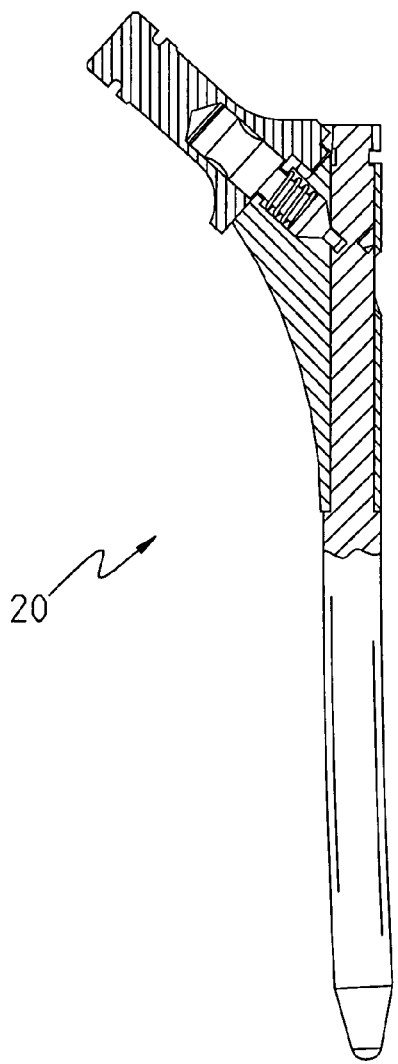
FIG. 8 is a front, partially sectional view of the modular trial assembly of FIG. 1 in an assembled state.
Figure 9:
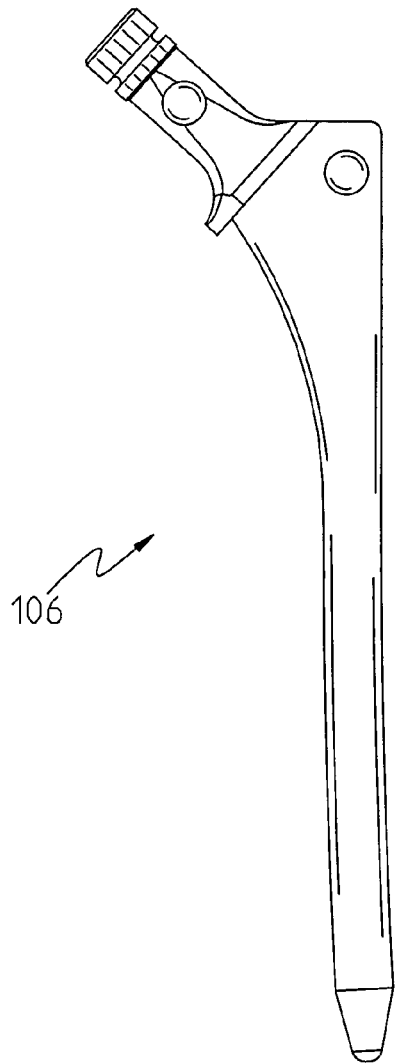
FIG. 9 is a front view of the prosthesis for which the assembled modular trial assembly of FIG. 8 trials.

At this point, the modular trial assembly 20 is fully assembled, as shown in FIG. 8. An implant 106, for which the assembly 20 trials, is shown in FIG. 9. As can be seen in a comparison of FIGS. 8 and 9, the assembly 20 closely mimics the size and shape of the implant 106.

Figure 10:
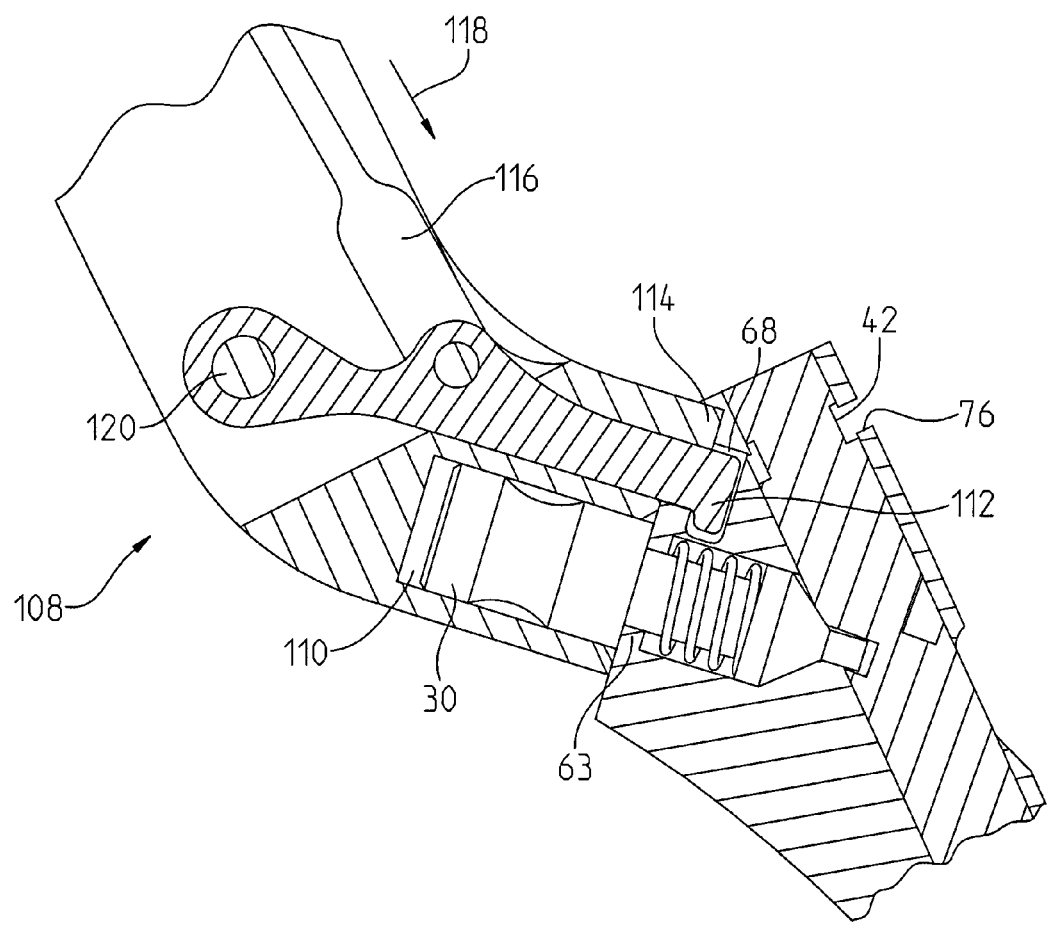
FIG. 10 is a front, partially sectional, fragmentary view of one embodiment of a handling tool used to place and/or extract the assembled combination of the body and stem of FIG. 1.

Before the neck 32 is placed on the body 24, the assembled combination of the body 24 and the stem 22 can be placed into the medullary canal of the reamed out femur by use of a handling tool 108 shown in FIG. 10. The tool 108 includes a cavity 110, an L-shaped latch 112, and a fin 114 that emulate the like features of the neck 32. The stud 30 can thus be received in the cavity 110, the L-shaped latch 112 can reside within the L-shaped cavity slot 68, and the fin 114 can slide into the linear slot 74.

Figure 11:
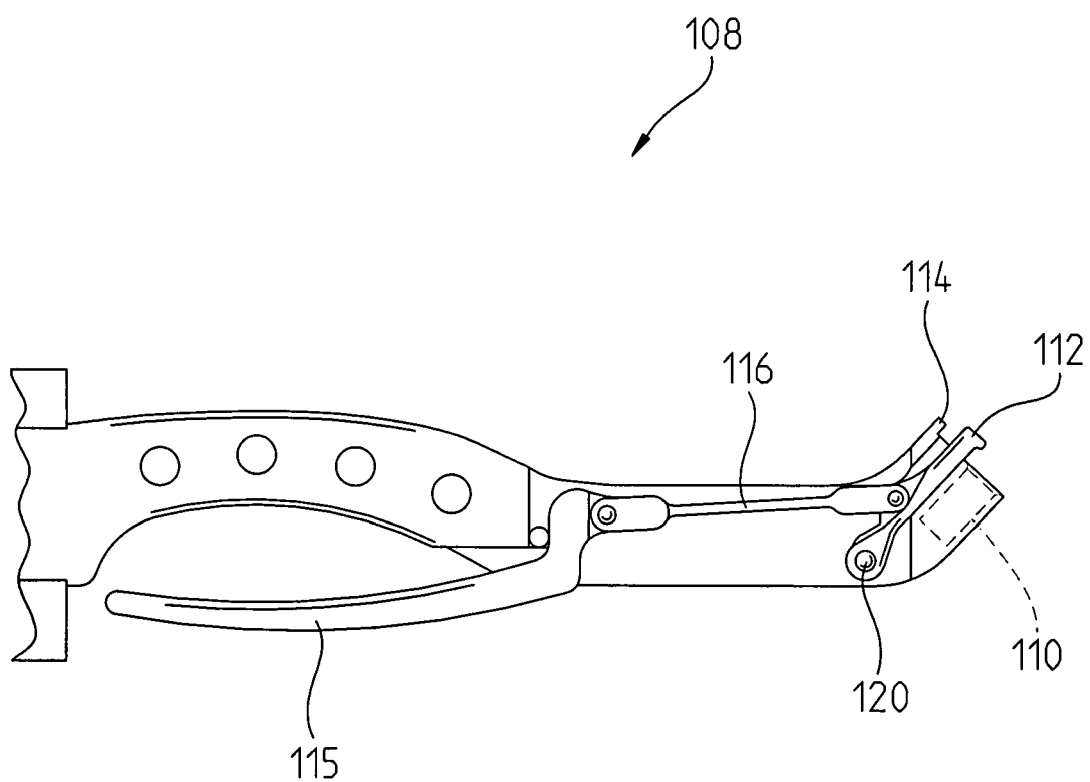
FIG. 11 is a plan, fragmentary view of the handling tool of FIG. 10.

During use, a first step in attaching the tool 108 to the body 24 includes aligning the tool 108 to the body 24 with a trigger 115 (FIG. 11) in an unsqueezed or unactuated position. Thus, a simultaneous alignment of the cavity 110 with the stud 30, the latch 112 with the slot 68, and the fin 114 with the slot 74 can be achieved. With the above elements simultaneously aligned, the tool 108 is advanced onto the body 24 such that the stud 30 is received in the cavity 110, the latch 112 is received in the slot 68, and the fin 114 is received in the slot 74. The trigger 115 is then squeezed or otherwise actuated to push a connecting rod 116 in a direction 118, thereby pivoting the latch 112 attached to the rod 116 about a pivot 120. Thus, the distal end of the latch 112 is hooked or latched into the L-shaped slot 68, as shown in FIG. 10. With the tool 108 thus attached to the body 24, the tool 108 can be used to insert the assembled combination of the body 24 and the stem 22 into the reamed out femur.

Figure 12:
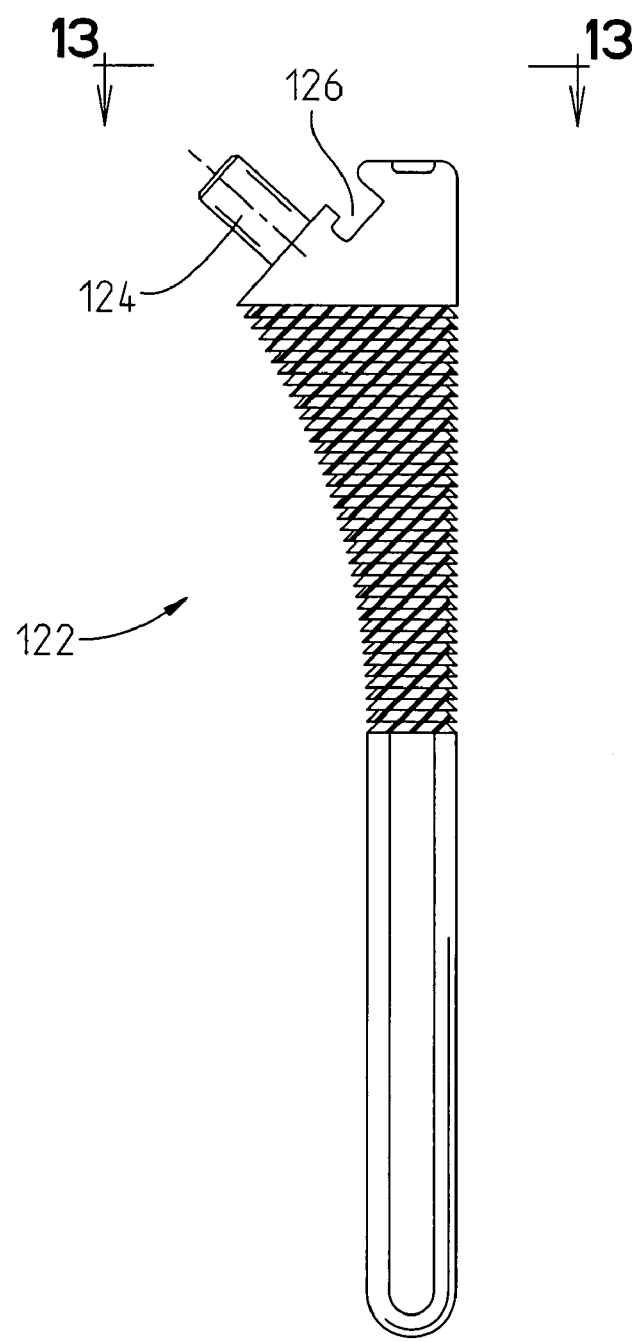
FIG. 12 is a front view of a broach that can be used with the handling tool of FIG. 10.

By using a procedure substantially the reverse of that described above, the tool 108 can also be used to extract the assembled combination of the body 24 and the stem 22 from the reamed out femur. Another tool (not shown) is placed in the aligned slot 76 and groove 42 during the extraction process. Further, the tool 108 can also place or extract a broaching apparatus 122 (FIG. 12), which is used in the reamed out femur.

Figure 13:
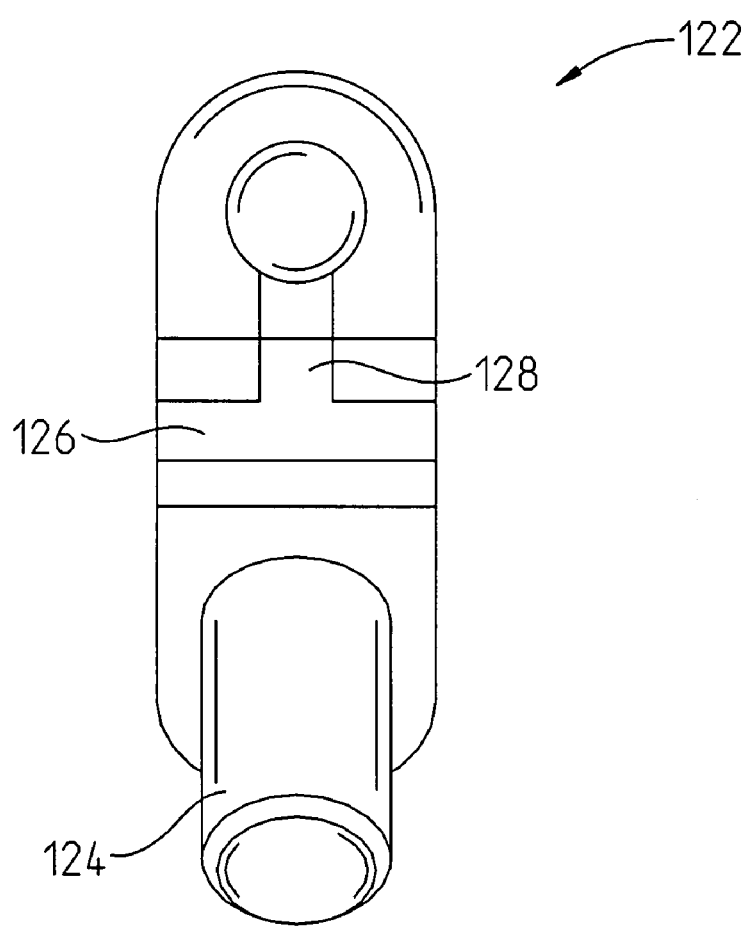
FIG. 13 is a top view of the broach of FIG. 12 along line 13-13.

The proximal end of the broaching apparatus 122 is configured similarly to the proximal end 54 of the body 24 for connection to the tool 108. More particularly, the broaching apparatus 122 includes a projection 124, an L-shaped slot 126, and a linear slot 128 (FIG. 13) for coupling with the cavity 110, the L-shaped latch 112, and the fin 114, respectively, of the tool 108.

It is also possible, in another embodiment, for the trial body 24 of the modular trial assembly 20 to be provided with serrated teeth, similarly to the broaching apparatus 122. Thus, the modular trial assembly 20 can function both as a trial assembly and as a broaching device.

Figure 14:
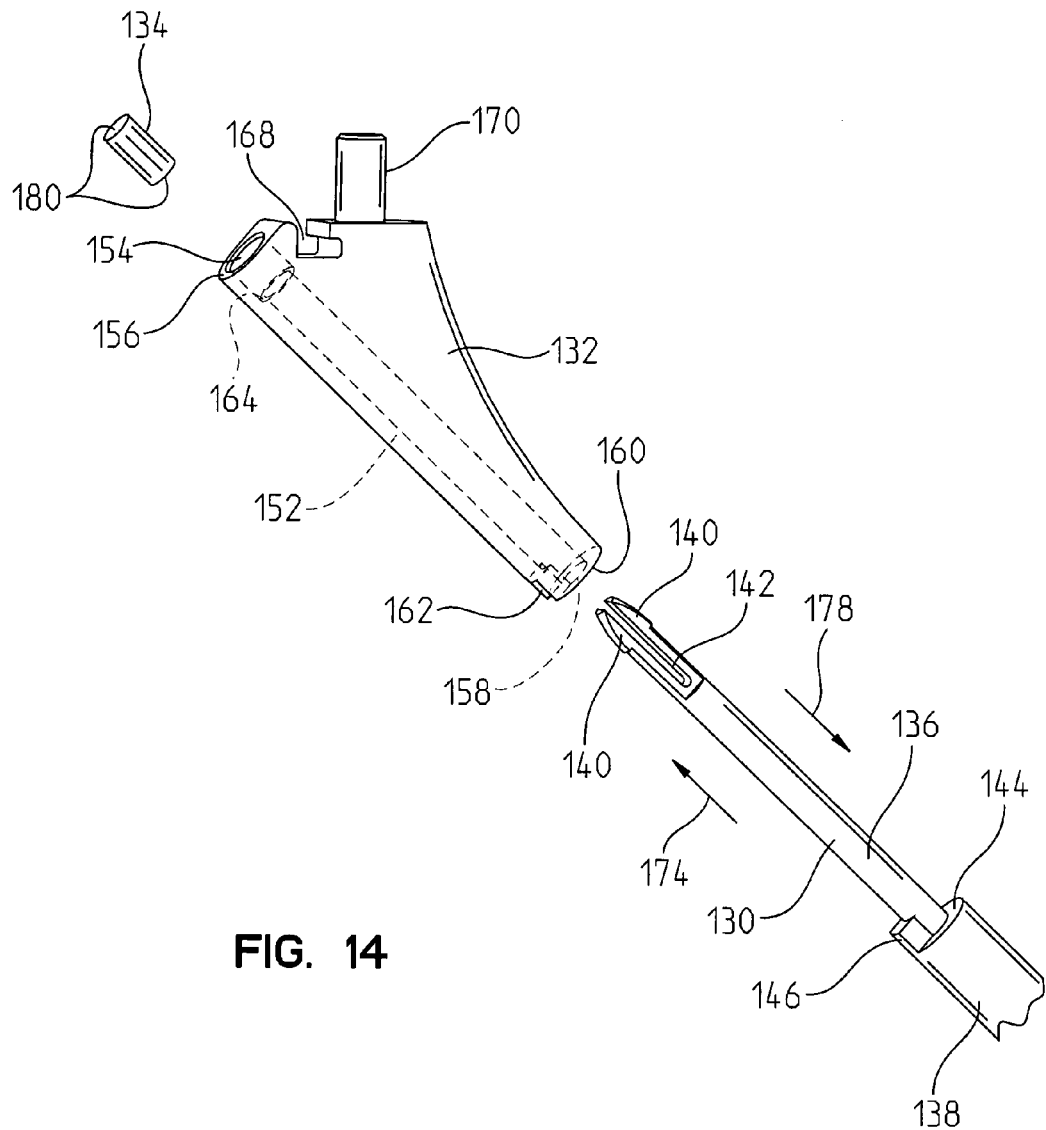
FIG. 14 is a perspective, partially sectional, fragmentary view of another embodiment of a body and a stem, and an unlocking tool of the present invention.

In another embodiment (FIG. 14) a stem 130 is attachable to a body 132. An unlocking tool 134 unlocks the stem 130 from the body 132 so that the stem 130 can be separated from the body 132.

Figure 15:
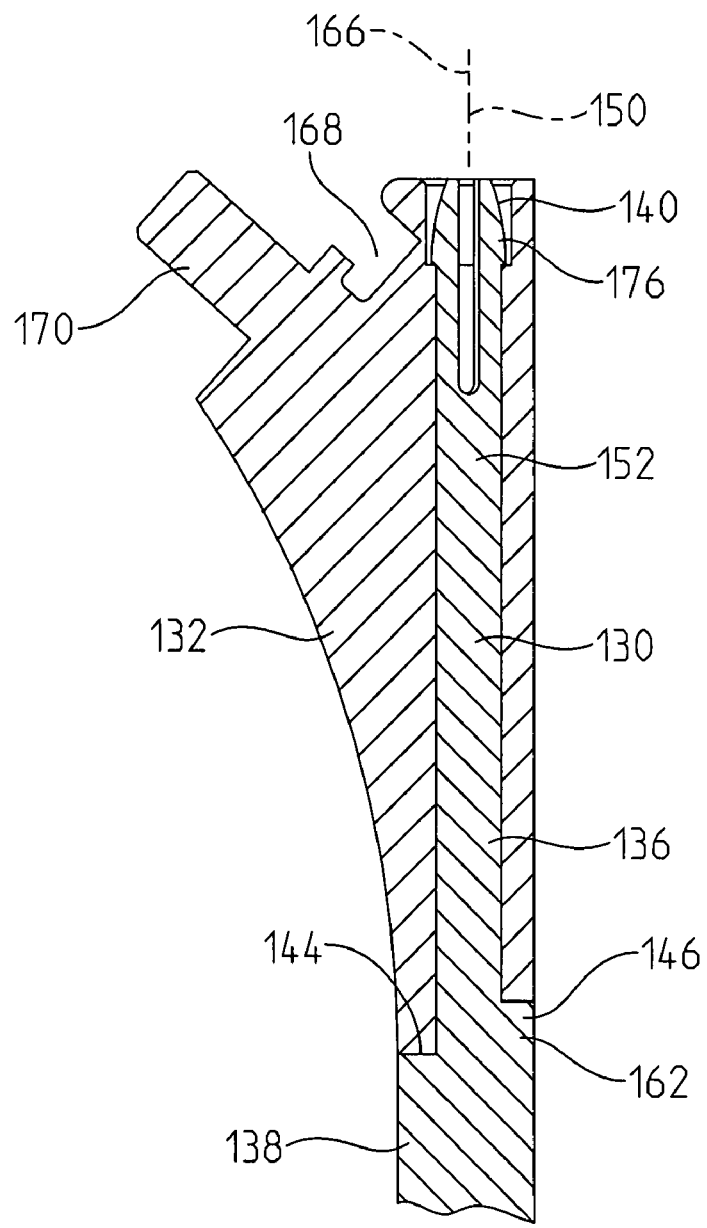
FIG. 15 is a front, sectional, fragmentary view of the body and stem of FIG. 14 in an assembled state.
Figure 16:
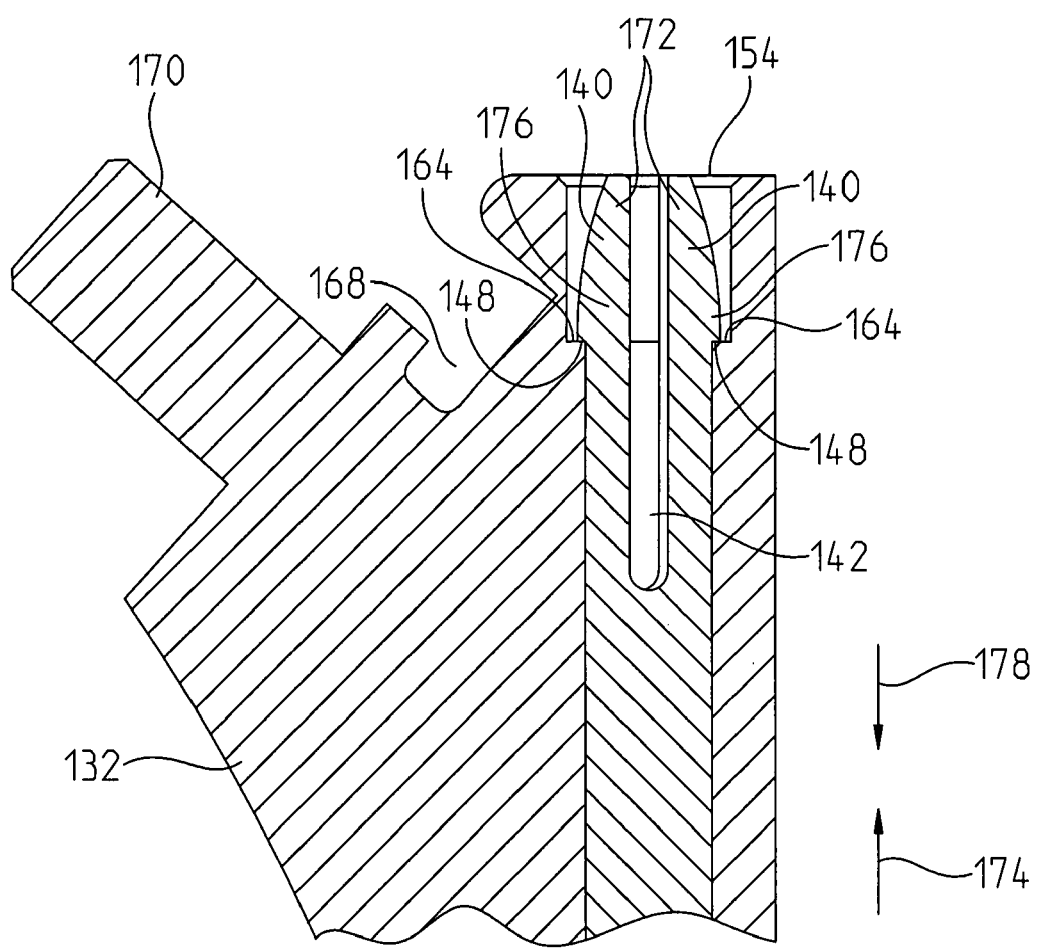
FIG. 16 is an enlarged view of the proximal ends of the body and stem of FIG. 14 in an assembled state.

The stem 130 includes a proximal section 136 and a distal section 138 for implantation in a bone. The proximal section 136 includes two resilient members in the form of opposing tapered prongs 140. The prongs 140 are separated by a gap 142. A proximal end 144 of the distal section 138 includes a projection or tab 146, best seen in FIG. 15. Each of the prongs 140 includes a latch 148 (FIG. 16) where the surface of the prong 140 is perpendicular to a longitudinal axis 150 of the stem 130.

The body 132 includes a through channel 152 having a proximal opening 154 at a proximal end 156 of the body 132, and a distal opening 158 at a distal end 160 of the body 132. The width or diameter of the opening 154 of the through channel 152 at the distal end 160 is greater than the width or diameter of the proximal section 136 of the stem 130, but is less than the width or diameter of the proximal end 144 of the distal section 138 of the stem 130. The distal end 160 includes a recess or cavity 162 in communication with the through channel 152. The cavity 162 is sized to receive the tab 146.

The through channel 152 includes an annular catch 164 where the surface defining the through channel 152 is perpendicular to a longitudinal axis 166 of the through channel 152. The diameter or width of the through channel 152 above, or disposed proximally of, the catch 164 is greater than the diameter or width of the through channel 152 below, or disposed distally of, the catch 164. The proximal end of the body 132 includes an L-shaped slot 168 and a projection 170 for unattached, nonrotatable coupling to a neck (not shown), as discussed in detail with regard to the previous embodiment.

During use, thin portions 172 of the prongs 140 are inserted into the distal opening 158 of the through channel 152. As the prongs 140 move in a proximal direction 174 through the through channel 152, thick portions 176 of the prongs 140 engage the wall of the through channel 152, and the prongs 140 are biased toward each other by the wall of the through channel 152. The stem 130 is rotated, if necessary, about its axis 150 such that the tab 146 is aligned with the cavity 162 of the body. Farther advancement of the stem 130 in the proximal direction 174 results in the tab 146 being received in the cavity 162. The coupling of the tab 146 and the cavity 162 prevents the stem 130 from rotating about its axis 150 within the through channel 152.

When the latches 148 of the prongs 140 move past the catch 164 of the through channel 152 in proximal direction 174, the prongs 140 spring outwardly and are no longer biased by the wall of the through channel 152. At this point, the proximal end 144 of the distal section 138 engages the distal end 160 of the body 132, thereby limiting further movement of the prongs 140 in the proximal direction 174.

If an attempt is now made to move the stem 130 in a distal direction 178, opposite to the proximal direction 174, the latches 148 of the prongs 140 latch onto the catch 164 and prevent the prongs 140 from passing by the catch 164 in the distal direction 178. Thus, the stem 130 is locked to the body 132. More particularly, the stem 130 is prevented from moving in either of directions 174, 178, and is prevented from rotating about its axis 150.

The unlocking tool 134 is a hollow, annular device with two open opposite ends 180. In order to unlock the stem 130 from the body 132, one of the ends 180 is inserted through the proximal opening 154 of the through channel 152. The open end 180 becomes seated over the thin portions 172 of the prongs 140. Farther movement of the tool 134 in the distal direction 178 causes the open end 180 to bias the two prongs 140 toward one another such that the latches 148 are no longer latched on the catch 164. The tool 134 can be sized such that the open end 180 becomes seated on the catch 164. The stem 130 can then be pulled in the distal direction 178 by its distal section 138 and can be withdrawn from the through channel 152.

Figure 17:
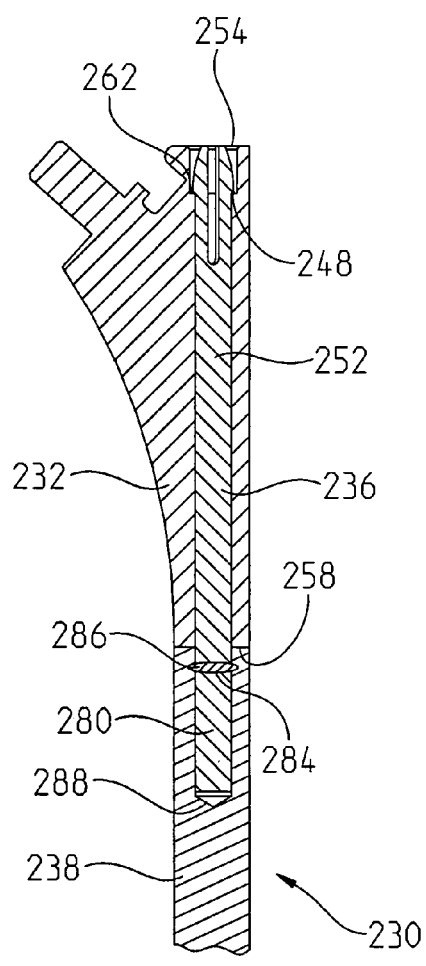
FIG. 17 is a front, sectional, fragmentary view of another embodiment of a body and a stem in an assembled state.
Figure 18:
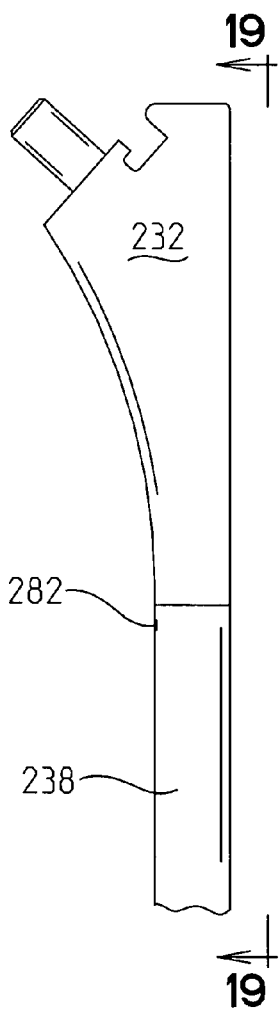
FIG. 18 is a front, fragmentary view of the body and stem of FIG. 17.
Figure 19:
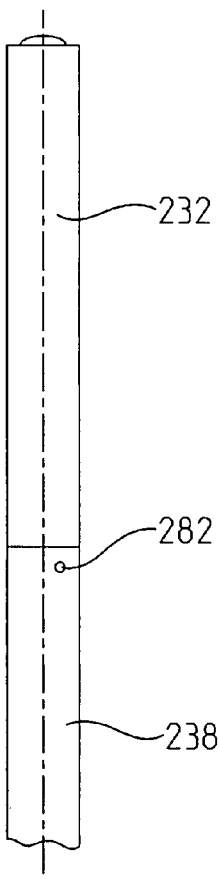
FIG. 19 is a side, fragmentary view of the body and stem of FIG. 18 along line 19-19.

In another embodiment (FIG. 17), a body 232 is attached to a stem 230 of two-piece construction. That is, the stem 230 has a proximal section 236 that is detachable from the distal section 238. The distal section 238 includes a bore 280 for receiving the distal end of the proximal section 236. The distal section 238 also includes a throughhole 282, best seen in FIGS. 18 and 19, extending through the bore 280. The throughhole 282 can be aligned with a throughhole 284 in the distal end of the proximal section 236 for receiving a pin 286 in each of the throughholes 282, 284. Thus, the pin 286 attaches the proximal section 236 and the distal section 238 of the stem 230.

After the proximal section 236 and the distal section 238 of the stem 230 have been attached by insertion of the pin 286, the stem 230 can be locked to the body 232 by the method described above with regard to FIGS. 14-16. Alternatively, it is also possible to insert the proximal section 236 through a proximal opening 254 of the through channel 252 before the proximal section 236 has been attached to the distal section 238. That is, the proximal section 236 can be inserted through the proximal opening 254, distal end first, until the latches 248 come to rest on or latch onto the catch 262. At this point, a distal end 288 of the proximal section 236 extends out of the distal end 258 of the body 232. The distal section 238 is coupled to the proximal section 236 by aligning the bore 280 with the distal end 288 of the proximal section 236 and receiving the distal end 288 in the bore 280. The pin 286 is inserted through the throughholes 282, 284 in order to attach the proximal section 236 to the distal section 238.

It should be appreciated that the modular trial assembly described herein is for use during performance of a joint replacement procedure such as a hip replacement procedure. Therefore, although the present invention is herein described in regard to performance of an exemplary hip replacement procedure, certain of the concepts of the present invention may be utilized in regard to replacement procedures at numerous other joint locations throughout the body.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the present invention and associated method described herein. It will be noted that alternative embodiments of the modular trial assembly and associated method of the present invention may not include all of the features described yet still benefit from at least some of the advantages of such features. Those of ordinary skill in the art may readily devise their own implementations of a modular trial assembly and associated method that incorporate one or more of the features of the present invention and fall within the spirit and scope of the present invention as defined by the appended claims.

What is claimed is:

1. A prosthetic trial for a joint prosthesis, comprising:
   a stem having a proximal section and a distal section configured for implantation in a bone;
   a body including a first channel configured to receive at least said proximal section of said stem;
   a neck configured to be coupled to said body, said neck defining a cavity; and
   a locking mechanism at least partially disposed within said body and configured to be at least partially positioned within said cavity, said locking mechanism biased into a locking position in which said locking mechanism locks said stem within said first channel of said body and accessible outside said body to be pulled into a releasing position to unlock said stem from said body.

2. The trial of claim 1, wherein said body includes a second channel, said locking mechanism being at least partially disposed within said second channel.

3. The trial of claim 2, wherein said second channel intersects said first channel.

4. The trial of claim 1, wherein said stem includes a recess receiving at least a portion of said locking mechanism when said locking mechanism is in the locking position.

5. The trial of claim 4, wherein said locking mechanism includes a spring and a projection, said spring biasing said projection into said recess of said stem.

6. The trial of claim 5, wherein said spring is disposed within said second channel.

7. The trial of claim 5, wherein said second channel includes a shoulder, said locking mechanism including a head attached to said projection, a first end of said spring being seated against said shoulder, a second end of said spring engaging said head.

8. The trial of claim 5, wherein said locking mechanism includes a stud attached to said projection, said stud being configured to be pulled into the releasing position, the projection being disposed out of said recess when said stud is in the releasing position.

9. The trial of claim 8, wherein said locking mechanism includes:
a head attached to said projection; and
a shaft interconnecting said head and said stud, said spring substantially surrounding said shaft.

10. The trial of claim 9, wherein said second channel includes a shoulder, said stud being seated against said shoulder.

11. A prosthetic trial for a joint prosthesis, comprising:
a body;
a stem separate from said body;
a neck separate from said body and said stem; and
a locking mechanism at least partially disposed within said body, said locking mechanism operable to lock said stem to said body and unattachedly couple said neck to said body,
wherein said body includes a through channel extending from a lateral side of said body to a medial side of said body, said locking mechanism being at least partially disposed within said channel.

12. The trial of claim 11, wherein said neck includes a first recess, said locking mechanism including a stud received in said first recess to thereby couple said neck to said body.

13. The trial of claim 12, wherein said stem includes a second recess, said locking mechanism including a second projection received in said second recess for locking said body to said stem.

14. The trial of claim 13, wherein said locking mechanism includes a spring biasing said second projection into said second recess.

15. The trial of claim 14, wherein said body includes a shoulder disposed in said through channel, at least one of said stud and said spring being seated on said shoulder.

16. A prosthetic trial for a joint prosthesis, comprising:
a stem with a longitudinal axis:
a neck having a first projection and a second projection; and
a body assembly for receiving the stem and including:
a first recess with a lower lip configured to receive the first projection such that when the first projection is received within the first recess, the first projection rests on the lower lip and the neck is constrained from lineal movement along the longitudinal axis of the stem; and
a second recess configured to receive the second projection such that when the second projection is received within the second recess, the neck is constrained from rotational movement with respect to the body assembly.

17. The prosthetic trial of claim 16, wherein:
the second recess is configured to receive the second projection such that when the second projection is received within the second recess, the neck is constrained from rotational movement with respect to the body assembly about an axis divergent from the longitudinal axis of the stem.

18. The prosthetic trial of claim 16, wherein:
the body assembly further comprises a third projection; and
the neck further comprises a third recess configured to receive the third projection such that when the third projection is received by the third recess, movement between the body and the neck is constrained.

19. The prosthetic trial of claim 18, further comprising:
a stem configured to extend at least partially into the body assembly; and
a locking mechanism at least partially disposed within said body assembly, said locking mechanism operable to lock said stem within said body assembly, and wherein the locking mechanism comprises the third projection.

20. The prosthetic trial of claim 19, wherein the locking mechanism comprises a pin operable to lock said stem within said body assembly.

21. The prosthetic trial of claim 16, wherein the neck is unattachedly coupled to the body assembly.

22. A prosthetic trial, comprising:
a stem having a proximal section and a distal section, the distal section configured for implantation in a bone;
a body including a channel configured to receive the proximal section of the stem;
a locking mechanism including
a locking member movable between (i) a first position in which the locking member allows linear movement of the stem within the channel of the body, and (ii) a second position in which the locking member prevents linear movement of the stem within the channel of the body, and
a biasing member configured to bias the locking member toward the second; and
a neck for coupling with the body such that access to the locking mechanism is constrained.

23. The prosthetic trial of claim 22, wherein:
the stem includes a recess; and
the locking member comprises a protuberance configured to fit within the recess, such that when the stem is within the channel and the recess is aligned with the protuberance, the biasing member biases the protuberance into the recess.

24. The prosthetic trial of claim 22, wherein the locking mechanism further comprises:
a stud accessible from external the body and movable between a third position and a fourth position and configured such that when the stud is in the third position, the locking member is in the first position and when the stud is in the fourth position the locking member is in the second position.

25. The prosthetic trial of claim 24, wherein
the neck includes a recess configured such that when the stud is in the fourth position and the neck is coupled with the body, at least a portion of the locking mechanism is within the recess.

26. The prosthetic of claim 22, wherein:
the body further comprises a slot; and
the stem comprises a fin located on the proximal end and configured to fit within the slot, such that when the fin is within the slot, rotational movement of the stem within the channel is prevented.

27. The prosthetic of claim 26, wherein
the neck includes a fin configured to fit within the slot.

28. A prosthetic system kit, comprising:
a prosthetic trial for a joint prosthesis;
a broaching device configured to broach a bone that is to receive said joint prosthesis; and
a handling tool operable on both of said trial and said broaching device,
wherein the prosthetic trial comprises a body with a stud and a slot; and
wherein the broaching device comprises a fin configured to fit within the slot and a cavity configured to accept the stud, such that when the fin is within the slot and the stud is within the cavity, rotational movement of the broaching device with respect to the body is prevented.

* * * * *